(12) United States Patent
LaVay et al.

(10) Patent No.: US 7,638,116 B2
(45) Date of Patent: Dec. 29, 2009

(54) POLYGLYCEROL DIMER POLYESTER RESINS

(75) Inventors: Carter LaVay, Riverside, CT (US); Anthony J. O'Lenick, Jr., Dacula, GA (US)

(73) Assignee: Zenitech LLC, Old Greenwich, CT (US)

( * ) Notice: Subject to any disclaimer, the term of this patent is extended or adjusted under 35 U.S.C. 154(b) by 0 days.

(21) Appl. No.: 11/978,041

(22) Filed: Oct. 29, 2007

(65) Prior Publication Data

US 2009/0110652 A1    Apr. 30, 2009

(51) Int. Cl.
*A61Q 5/00* (2006.01)
*A61K 47/00* (2006.01)

(52) U.S. Cl. ............... 424/70.11; 424/78.37; 424/401; 514/785; 516/21; 516/22; 516/33; 516/115; 516/124; 528/271; 528/272; 528/295.3; 528/295.5; 528/302

(58) Field of Classification Search ............... None
See application file for complete search history.

(56) References Cited

U.S. PATENT DOCUMENTS

| 1,424,137 | A | | 7/1922 | Weisberg | |
|---|---|---|---|---|---|
| 6,800,275 | B1 | * | 10/2004 | O'Lenick, Jr. | 424/70.11 |
| 2005/0031580 | A1 | * | 2/2005 | Allef et al. | 424/78.37 |
| 2007/0134182 | A1 | * | 6/2007 | Shimizu et al. | 424/64 |

OTHER PUBLICATIONS

Plusman, Polyglycerols Happi Nov. 2004 p. 94-97.

* cited by examiner

*Primary Examiner*—Vasu Jagannathan
*Assistant Examiner*—Gennadiy Mesh

(57) ABSTRACT

The present invention relates to a series of novel polyesters that are prepared by crosslinking polyglycerol and dimer acid. The nature of the water loving polyglycerol group as well as the fact that a C-36 fatty diacid is used in preparation of the products results in unique products.

19 Claims, No Drawings

POLYGLYCEROL DIMER POLYESTER RESINS

BACKGROUND OF THE INVENTION

1. Field of the Invention

The present invention relates to a series of novel polyesters prepared by crosslinking polyglycerol molecules with dimer acid. The nature of the water loving polyglycerol group and the C-36 fatty diacid is used in preparation of the products results in unique products. The selection of the proper ratio of hydroxyl to carboxyl group determines the degree of crosslinking and the cosmetic aesthetics of the resulting material.

2. Arts and Practices

Polyglycerol compounds are well known materials. They are made by the condensation reaction of glycerin. The resulting products are polar and possess several un-reacted hydroxyl groups on the polyglycerol. The number of glycerin molecules condensed in the reaction is referred to as the dp (or degree of polymerization).

Polyglycerol esters are aloe well known. They are the product of the esterification reaction of polyglycerol and fatty acids. Water is the by-product and a fatty ester group is added. U.S. Pat. No. 5,721,305 issued Feb. 24, 1998 to Eshuis, et al. entitled Polyglycerol production teaches how polyglycerol is made.

U.S. Pat. No. 3,936,391 issued Feb. 3, 1976 to Gabby entitled Hydrated polyglycerol ester composition teaches An polyglycerol ester emulsifier is prepared by heating a polyglycerol ester having 3 to 10 glycerol units and 1 to 2 saturated fatty acyl ester groups each having 16-20 carbon atoms, glycerol and water at a temperature of from 125 F to 135 F. until a homogeneous paste-like consistency is imparted thereto.

Still another patent is U.S. Pat. No. 5,674,475 issued Oct. 7, 1997 to Dahms entitled "Emulsifier composition based on polyglycerol ester" which teaches an emulsifier composition is a mixture of polyglycerol fatty acid ester and the lactylate of a fatty acid) or its salt and is used to manufacture a wide range of different O/W emulsions.

U.S. Pat. No. 1,424,137, issued July 1922 to Weisberg, entitled polyglycerol resins discloses a polyglycerol ester of an aromatic dibasic acid used in shellac. This patent, incorporated herein by reference, addresses solid resins made in solvent. While lacking the critical dimer acid component and producing hard rather than soft esters, this patent shows the state of the art in resins.

None of the references understood the desirability of incorporating a polyglycerol group with dimer acid to make a heretofore unknown polymer allowing for the alteration of the solubility in oils, water, and to make heretofore unavailable materials having outstanding lubrication properties when applied to hair, skin and fibers.

THE INVENTION

Object of the Invention

It is the object of the present invention to provide novel polyesters based upon three substituents; dimer acid, the fatty portion, and polyglycerol, the water-loving portion. This class of polyesters will deposit on fibrous materials from aqueous systems. The key to the deposition is the balance between the three groups that improves solubility that has been heretofore not understood.

While not wanting to be limited to a specific theory of the improved deposition, the molecular size and configuration results in a product which when placed into water forms laminar sheets rather than micelles. This results in the lowest free energy of the system being when the polymer, albeit soluble in water, is out of solution. The fewest hydrogen bonds between water molecules are disrupted when the polymer is absent. This is exactly the phenomenon which occurs when oil floats on water.

SUMMARY OF THE INVENTION

The present invention relates to a series of novel polyesters that are prepared by crosslinking polyglycerol and dimer acid. The nature of the water loving polyglycerol group as well as the fact that a C-36 fatty diacid is used in preparation of the products results in unique products. The selection of the proper ratio of hydroxyl to carboxyl group determines the degree of crosslinking and the cosmetic aesthetics of the resulting material.

The compounds of this invention are made by the esterification of dimer acid ester, and polyglycerol, a polyhydroxy-containing compound. The resulting product has compatibility over those made lacking the combination of groups. This results in highly efficient deposition on the skin, hair and textile fiber.

The compounds of the present invention are made by the reaction of Dimer acid with polyglycerol at very specific ratios of hydroxyl to carboxy (acid) groups.

The present invention teaches a polyester made by the reaction of (a) dimer acid conforming to the following structure:

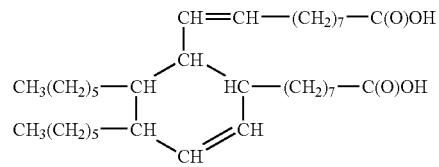

or hydrogenated dimer acid conforming to the following structure:

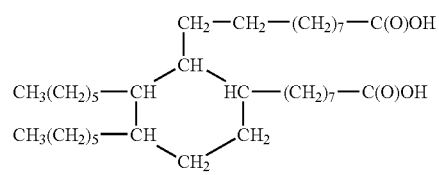

or mixtures thereof;

with (b) a polyglycerol conforming to the following structure;

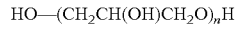

n is an integer ranging from 3 to 20.

The fact that the water soluble groups, oil soluble groups are present on the molecule results in unique solubility surfactant molecules, the solubility of which can be altered by changing the concentration of dimer acid, keeping its concentration low relative to hydroxyl groups thereby limiting crosslinking and providing a soft product with outstanding skin feel.

The present invention also teaches a process for conditioning hair skin and fiber which comprises contacting the hair skin of fiber with an effective conditioning concentration of a polyester made by the reaction of (a) dimer acid conforming to the following structure:

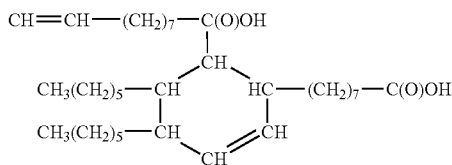

or hydrogenated dimer acid conforming to the following structure:

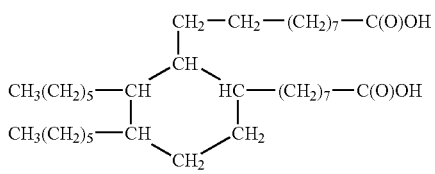

or mixtures thereof;

with (b) a polyglycerol conforming to the following structure;

n is an integer ranging from 3 to 20.

The process is highly efficient since the polyester has been carefully chosen to minimize crosslinking and consequently hardness of the resin. The result is the effective conditioning of hair in anionic systems at concentrations as low as 0.5% by weight.

PREFERRED EMBODIMENTS

In a preferred embodiment dimer acid source is dimer acid.

In another preferred embodiment dimer acid source is hydrogenated dimer acid.

In a preferred embodiment the mole ratio of hydroxyl groups on the polyglycerol to carboxyl groups on the dimer acid ranges from 2:1 to 4:1.

In preferred embodiment the mole ratio of hydroxyl groups on the polyglycerol to carboxyl groups on the dimer acid is 2:1.

In preferred embodiment the mole ratio of hydroxyl groups on the polyglycerol to carboxyl groups on the dimer acid is 3:1.

In preferred embodiment the mole ratio of hydroxyl groups on the polyglycerol to carboxyl groups on the dimer acid is 4:1.

In a preferred embodiment said effective conditioning concentration ranges between 0.1 and 10% by weight.

EXAMPLES

Example 1

Dimer Acid

Dimer acid is an item of commerce and is available from a variety of sources including Cognis Chemical Cincinnati Ohio. It conforms to the following structure:

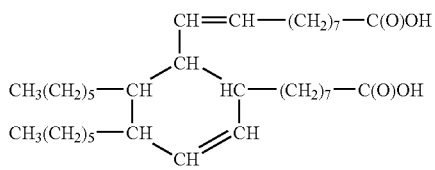

Example 2

Hydrogenated Dimer

Hydrogenated dimer acid is an item of commerce and is available from a variety of sources including Cognis Chemical Cincinnati Ohio. It conforms to the following structure:

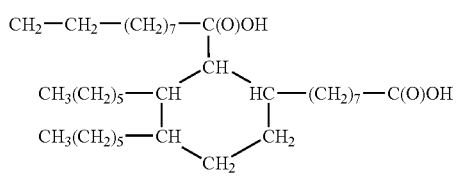

or mixtures thereof.

Polyglycerol

Polyglycerol compounds are commercially available from a variety of sources, including Phoenix Chemical Somerville, N.J. They conform to the following structure:

n is an integer ranging from 3 to 20.

| Example | n |
|---------|-----|
| 3 | 3 |
| 4 | 5 |
| 5 | 10 |
| 6 | 20 |

General Reaction Conditions

The esterification can be carried out without catalyst; however, when no catalysts are used reaction rates are less efficient. Standard esterification catalysts are generally used at concentrations of between 0.05% to 0.50% with a preferred range of 0.1% to 0.3%. Catalysts which are effective include but are not limited to; sulfuric acid, p-toluene sulfonic acid, methane sulfonic acid, tin metal, zinc metal, titanium metal, organo titianates, organo tin compounds, organo zinc compounds, zinc oxide, magnesium oxide, calcium oxide, etc. The most preferred catalyst is stannous oxylate. The reaction is conducted at between 140 and 240 C. under an inert nitrogen blanket. The nitrogen blanket preserves the color. Preferred temperature range is between 180 and 210 C. Water is removed from the reaction which is done using a nitrogen sparge or vacuum.

Example 13-23

Into a suitable round bottom, three neck flask equipped with a Dean Stark trap, a thermometer and a nitrogen sparge is added the 150.0 grams of dimer material (Example 1, 2 or mixtures thereof), the specified number of grams of the specified polyglycerol (Example 3-6). Next is added 0.25% by weight of the total batch charged of stannous oxylate. The reaction mass is blanketed with nitrogen, and heated to 180° C. and 200° C. under an inert nitrogen blanket. Once the reaction temperature reaches 120° C., water begins to boil off and is collected in the Dean Stark Trap. Within five to ten hours the theoretical water is collected off and the acid value is very low. The product is a clear liquid and is used without additional purification.

| Example | Dimer Acid Example | Polyglycerol Example | Grams | Hydroxyl:Carboxyl Ratio |
|---|---|---|---|---|
| Preferred Compounds | | | | |
| 13 | 1 | 3 | 120 | 2:1 |
| 14 | 1 | 4 | 195 | 3:1 |
| 15 | 1 | 5 | 280 | 4:1 |
| 16 | 1 | 6 | 144 | 2:1 |
| 17 | 2 | 3 | 280 | 4:1 |
| 18 | 2 | 4 | 144 | 2:1 |
| 20 | 2 | 5 | 216 | 3:1 |
| 21 | 2 | 6 | 280 | 4:1 |
| Less Preferred Compounds | | | | |
| 22 | 1 | 3 | 60 | 1:1 |
| 23 | 1 | 4 | 65 | 1:1 |
| 24 | 1 | 5 | 69 | 1:1 |
| 25 | 1 | 6 | 72 | 1:1 |

The preferred compounds (Examples 13-21) are yellow viscous liquids that have outstanding lubricants and emollients when applied to hair skin and fiber.

The less preferred compounds (Examples 12-25) are yellow high viscosity liquids that have lubricants and emollients properties but are somewhat tacky when applied to hair skin and fiber.

None of the compounds are solid materials like those disclosed in U.S. Pat. No. 1,424,137.

While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth hereinabove but rather that the claims be construed as encompassing all the features of patentable novelty which reside in the present invention, including all features which would be treated as equivalents thereof by those skilled in the art to which the invention pertains.

The invention claimed is:

1. A polyester made by esterification reaction consisting of the reaction of:
(a) dimer acid conforming to the following structure:

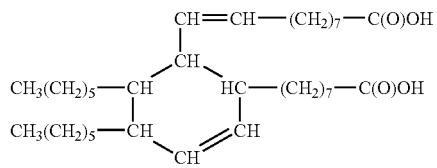

or hydrogenated dimer acid conforming to the following structure:

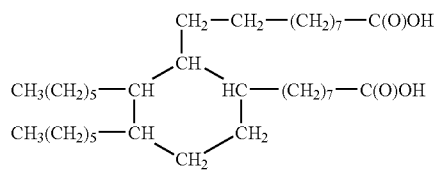

or mixtures thereof;
with
(b) a polyglycerol conforming to the following structure;

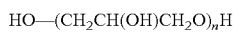

n is an integer ranging from 3 to 20.

2. The polyester of claim 1 wherein the mole ratio of hydroxyl groups on the polyglycerol to carboxyl groups on the dimer acid ranges from 2:1 to 4:1.

3. The polyester of claim 2 wherein said esterification reaction is conducted at a temperature of between 120° C. and 200° C. for five to 10 hours.

4. The polyester of claim 2 wherein said dimer acid source is dimer acid.

5. The polyester of claim 2 wherein said dimer acid source is hydrogenated dimer acid.

6. The polyester of claim 1 wherein the mole ratio of hydroxyl groups on the polyglycerol to carboxyl groups on the dimer acid is 2:1.

7. The polyester of claim 1 wherein the mole ratio of hydroxyl groups on the polyglycerol to carboxyl groups on the dimer acid is 3:1.

8. The polyester of claim 1 wherein the mole ratio of hydroxyl groups on the polyglycerol to carboxyl groups on the dimer acid is 4:1.

9. A process for conditioning hair skin and fiber which comprises contacting the hair skin of fiber with an effective conditioning concentration of a polyester made by the reaction consisting of the reaction of:
(a) dimer acid conforming to the following structure:

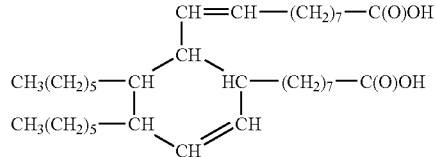

or hydrogenated dimer acid conforming to the following structure:

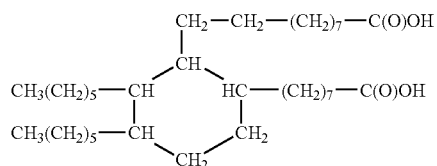

or mixtures thereof;
with
(b) a polyglycerol conforming to the following structure;

n is an integer ranging from 3 to 20.

10. The process of claim 9 wherein the mole ratio of hydroxyl groups on the polyglycerol to carboxyl groups on the dimer acid ranges from 2:1 to 4:1.

11. The process of claim 10 wherein said esterification reaction is conducted at a temperature of between 120° C. and 200° C. for five to 10 hours.

12. The process of claim 10 wherein said dimer acid source is dimer acid.

13. The process of claim 10 wherein said dimer acid source is hydrogenated dimer acid.

14. The process of claim 9 wherein the mole ratio of hydroxyl groups on the polyglycerol to carboxyl groups on the dimer acid is 2:1.

15. The process of claim 9 wherein the mole ratio of hydroxyl groups on the polyglycerol to carboxyl groups on the dimer acid is 3:1.

16. The process of claim 9 wherein the mole ratio of hydroxyl groups on the polyglycerol to carboxyl groups on the dimer acid is 4:1.

17. The process of claim 10 wherein said effective conditioning concentration ranges between 0.1 and 10% by weight.

18. The process of claim 10 wherein said dimer acid source is dimer acid.

19. The process of claim 10 wherein said dimer acid source is hydrogenated dimer acid.

* * * * *